US005457750A

United States Patent [19]

Ahn

[11] Patent Number: 5,457,750

[45] Date of Patent: Oct. 10, 1995

[54] METHOD AND DEVICE FOR REDUCING NOISES GENERATED AT AN INDOOR UNIT OF A SEPARATE TYPE ROOM AIR CONDITIONER PACKAGE

[75] Inventor: Byung H. Ahn, Busan, Rep. of Korea

[73] Assignee: Gold Star Company, Ltd., Seoul, Rep. of Korea

[21] Appl. No.: 281,527

[22] Filed: Jul. 27, 1994

Related U.S. Application Data

[63] Continuation of Ser. No. 141,416, Oct. 22, 1993, abandoned, which is a continuation of Ser. No. 810,055, Dec. 19, 1991, abandoned.

[30] Foreign Application Priority Data

Dec. 19, 1990 [KR] Rep. of Korea .................. 21099/1990

[51] Int. Cl.$^{6}$ ............................ A61F 11/06; H03B 29/00

[52] U.S. Cl. ............................................................ 381/71

[58] Field of Search ................................ 381/71, 94, 86; 181/206

[56] References Cited

U.S. PATENT DOCUMENTS

| | | | |
|---|---|---|---|
| 4,506,380 | 3/1985 | Matsui | 381/86 |
| 4,947,434 | 8/1990 | Ito | 381/71 |
| 5,010,576 | 4/1991 | Hill | 381/71 |
| 5,029,218 | 7/1991 | Nagayasu | 381/71 |
| 5,097,923 | 3/1992 | Ziegler et al. | 381/71 |
| 5,111,507 | 5/1992 | Nakaji | 381/71 |

FOREIGN PATENT DOCUMENTS

| | | | |
|---|---|---|---|
| 0207170 | 8/1990 | Japan | 381/71 |
| 1357330 | 6/1974 | United Kingdom | 181/206 |

*Primary Examiner*—Curtis Kuntz
*Assistant Examiner*—Ping W. Lee
*Attorney, Agent, or Firm*—Fish & Richardson

[57] ABSTRACT

A method of and a device for reducing noises generated at an exhaust grid of an indoor unit of separate type room air conditioner package includes speakers disposed at upper and lower sides of the exhaust grid, a sensor for sensing a noise condition at a main noise source, and a control device for analyzing the noise condition sensed by the sensor and emitting control noises through the speakers.

6 Claims, 12 Drawing Sheets

METHOD AND DEVICE FOR REDUCING NOISES GENERATED AT AN INDOOR UNIT OF A SEPARATE TYPE ROOM AIR CONDITIONER PACKAGE

This application is a file wrapper continuation of U.S. application Ser. No. 08/141,416, filed Oct. 22, 1993, which is a file wrapper continuation of U.S. application Ser. No. 07/810,055, filed Dec. 19, 1991, both now abandoned.

BACKGROUND OF THE INVENTION

1. Field of the Invention

This invention generally relates to a separate type room air conditioner package divided into an indoor unit and an outdoor unit, and more particularly to a method and a device for reducing noises generated at an exhaust port of the indoor unit of the room air conditioner package.

2. Description of the Prior Art

Generally, a separate type room air conditioner package is of the type shown in FIG. 10 of the accompanying drawings and broadly comprises an indoor unit 1 which is installed inside a building, and an outdoor unit 2 which is installed outside the building and connected to the indoor unit by connection pipes 3 to permit a cycle of a heat flow to be effected between the units.

The outdoor unit 2 includes a heat exchanger 4, a compressor 5 and a fan 6 and functions to produce cold air by means of circulation of a refrigerant.

On the other hand, the indoor unit 1 which is installed inside the building is of the general box type as shown in FIGS. 11 and 12 of the accompanying drawings and comprises an intake grid 10 disposed at its lower portion to suck indoor air, a heat exchanger 11 mounted within the unit in the region behind the intake grid 10, a centrifugal fan 12 disposed at the middle portion to compulsorily discharge into an exhaust duct 13 the air cooled by passing through the heat exchanger 11, and an exhaust grid 14 disposed at the upper portion to discharge into the interior of a room the cold air passed through the exhaust duct 13.

In addition, a control panel 15 comprising, for example, a power button, a printed circuit board, etc., for controlling the indoor unit 1 is disposed in the front of the middle portion where the centrifugal fan 12 is located.

In operation of the indoor unit thus constructed, when the indoor unit is switched on through operation of the control panel 15, the centrifugal fan 12 is actuated, so that the indoor air is sucked through the intake grid 10, then passes through the centrifugal fan 12, and is discharged through the exhaust grid 14 into the interior of the room, as shown by the arrows in FIG. 12. At this time, the indoor air of a higher temperature sucked through the intake grid 10 is changed into the cold air having a lower temperature by passing through the heat exchanger 11, so that the air conditioning of the room may be effected. In the indoor unit, noises are generated by flow of the air passing through the unit. The noises take the forms as shown in a noise waveform chart of FIG. 13, a corresponding vibration spectrum of FIG. 14, and noise waveform charts of FIG. 15 illustrating the noises generated at the left, the front and the right sides of the indoor unit. At this time, the dominant frequency band of the noise generated at the indoor unit is the low frequency band less than approximately 600 Hz, and a most violent noise is generated in the region of the exhaust duct. The reason why the noise generated in the region of the exhaust duct is most violent is that while sound pressure in the region is highest, it is difficult to accomplish absorption of the noise of the low frequency band in the exhaust area.

SUMMARY OF THE INVENTION

It is, therefore, an object of the present invention to provide a noise reduction device for an indoor unit of separate type room air conditioner package, which generates a control noise having an antiphase signal, thereby reducing noises generated at an exhaust port of the indoor unit and emitted to the interior of a room.

To achieve the above object, there is provided according to one form of the present invention a noise reduction device for an indoor unit of a separate type room air conditioner package, comprising speakers disposed at upper and lower sides of an upper exhaust grid of the indoor unit to emit control noises, sensing means disposed at a main noise source, i.e., a duct portion for sensing a noise condition, and a control means for analyzing the noise condition sensed by the sensing means and emitting the control noise of an antiphase in accordance with the analyzed factor through the speakers.

BRIEF DESCRIPTION OF THE DRAWINGS

The invention will now be described further, by way of example, with reference to the accompanying drawings, in which.

DESCRIPTION OF THE PREFERRED EMBODIMENT(S)

Figure 1:
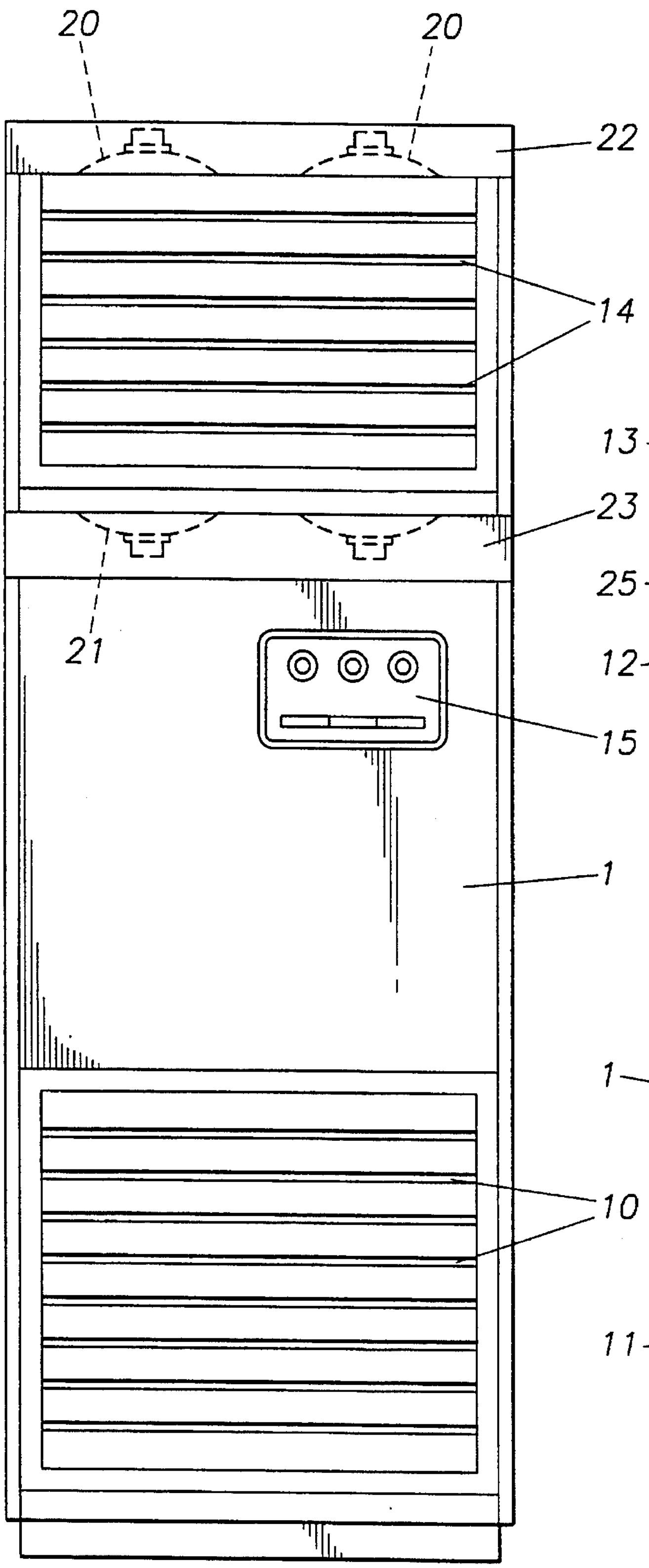
FIG. 1 is a front view of an indoor unit of a separate type room air conditioner package incorporating a noise reduction device according to one embodiment of the present invention.
Figure 2:
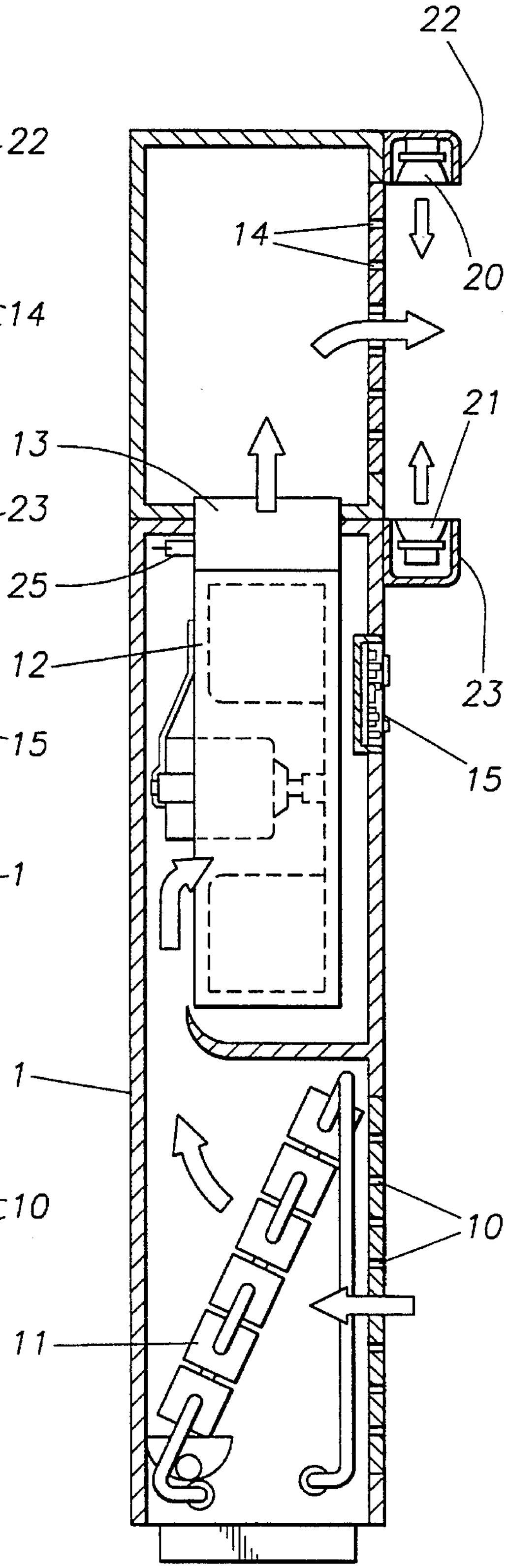
FIG. 2 is a vertical cross-sectional view of the indoor unit shown in FIG. 1.

FIGS. 1 and 2 illustrate front and cross-sectional views of an indoor unit of a separate type room air conditioner package incorporating the present invention. Because the basic construction and operation of the indoor unit are the same as those of the prior art described above, the detailed description of them are omitted herein to avoid duplication of explanation. Also, throughout the following description, the same elements as those of the prior art are designated by the same reference numerals.

In this embodiment, as shown in FIG. 2, upper and lower speakers 20 and 21 protected by upper and lower covers 22 and 23, respectively, are provided at upper and lower sides of an exhaust grid 14 disposed at an outlet side of an exhaust duct 13 of the indoor until 1. At this time, the upper and lower speakers 20 and 21 are disposed in pairs within each of the covers.

In addition, there is disposed at one side of the exhaust duct 13 above a centrifugal fan 12 a sensor 25 which is sensor means for sensing a noise condition.

Figure 9A:
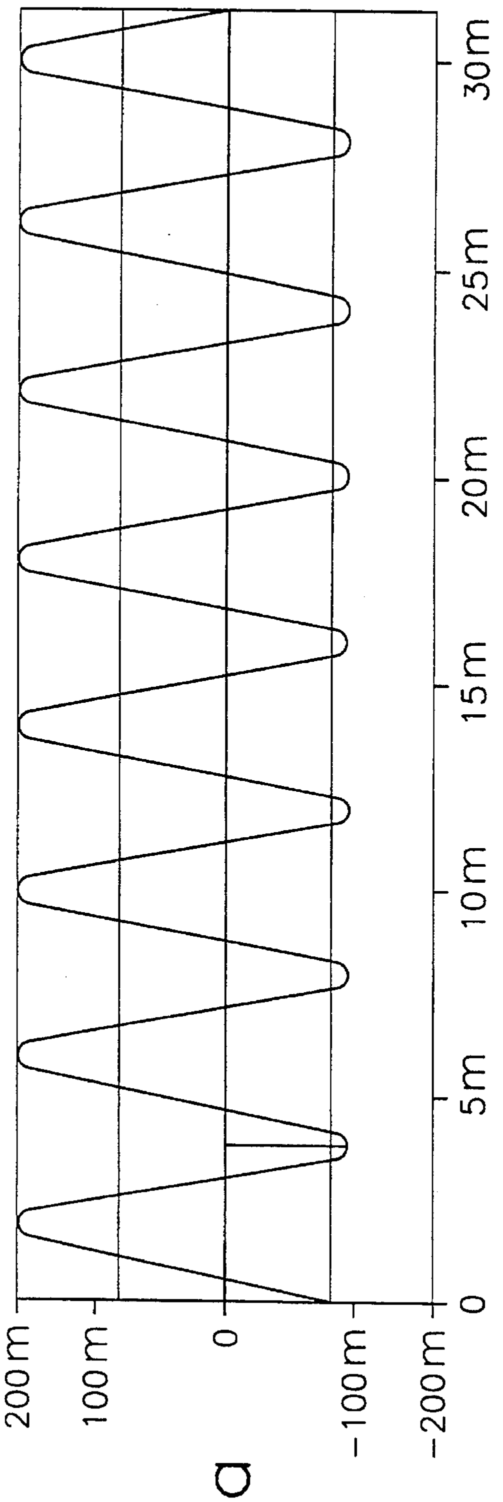
FIG. 9A being a waveform chart of the noise from the noise source.
Figure 9B:
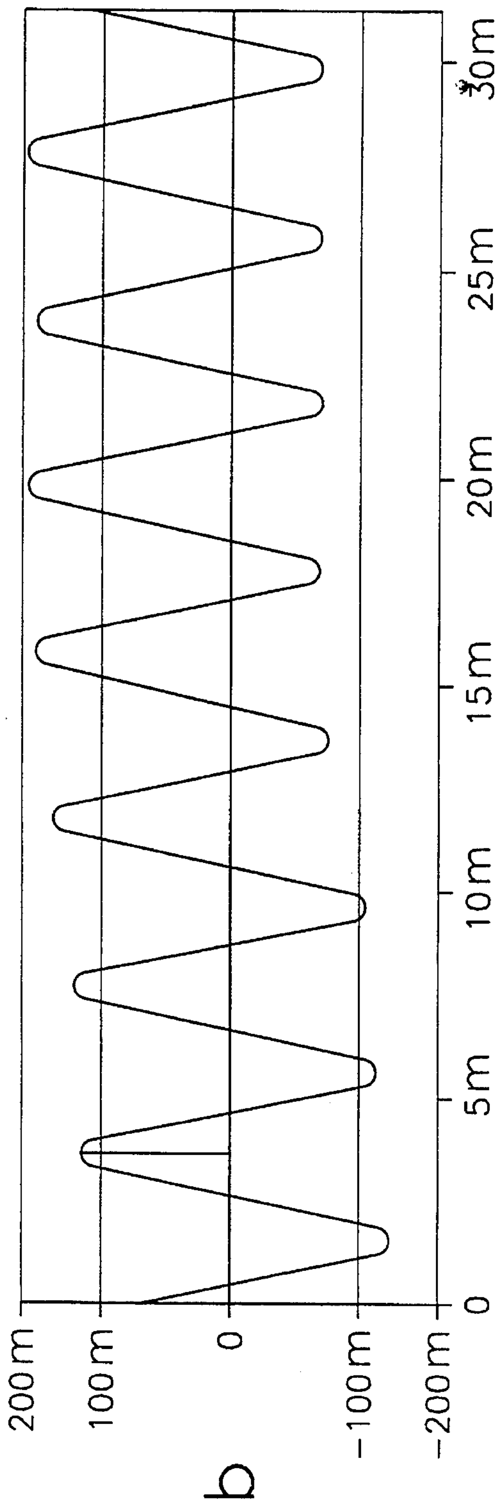
FIG. 9B being a waveform chart of the control noise emitted from the speaker.
Figure 10:
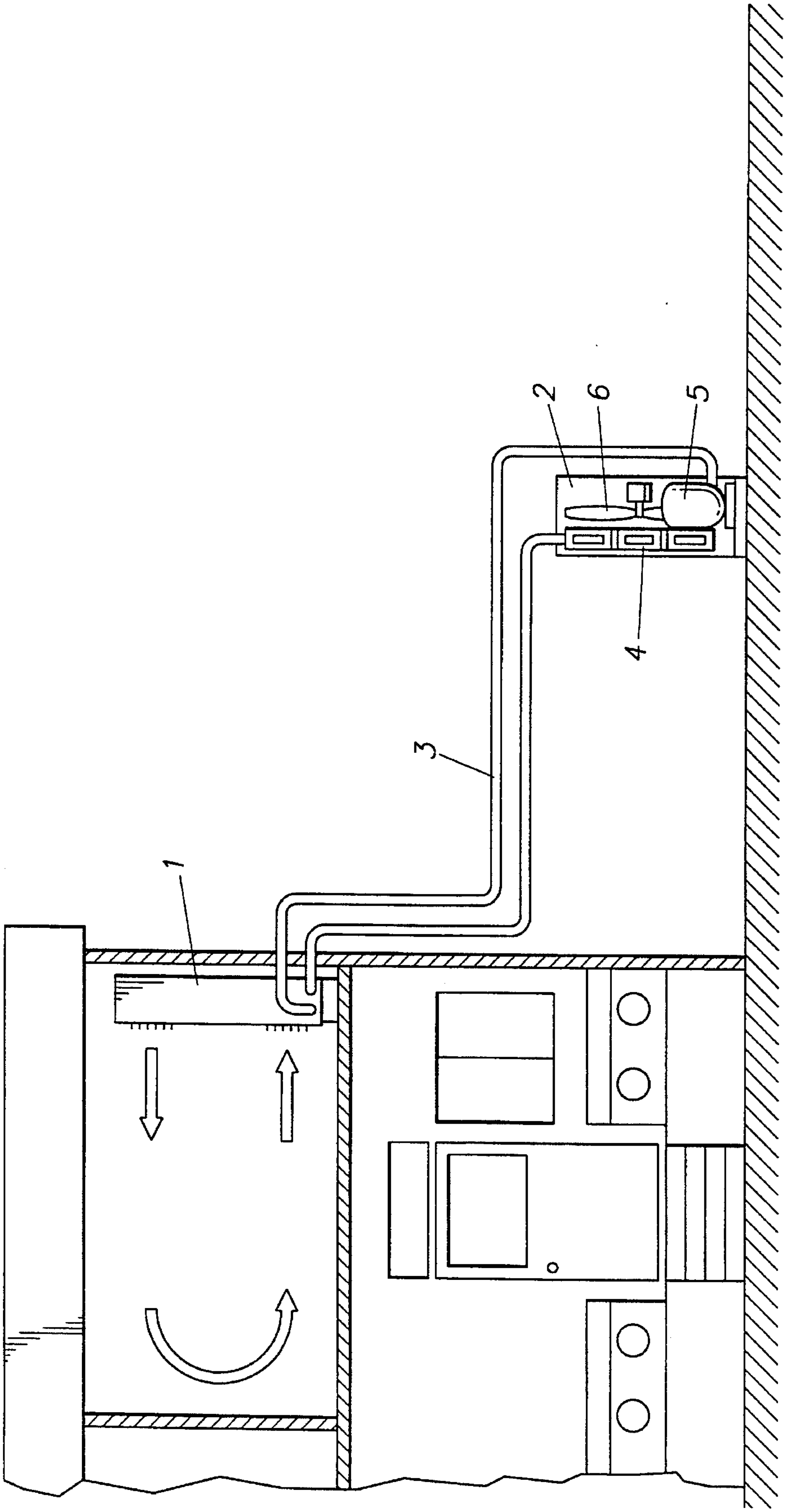
FIG. 10 is a schematic view showing the entire construction of a typical form of the separate type room air conditioner package.
Figure 11:
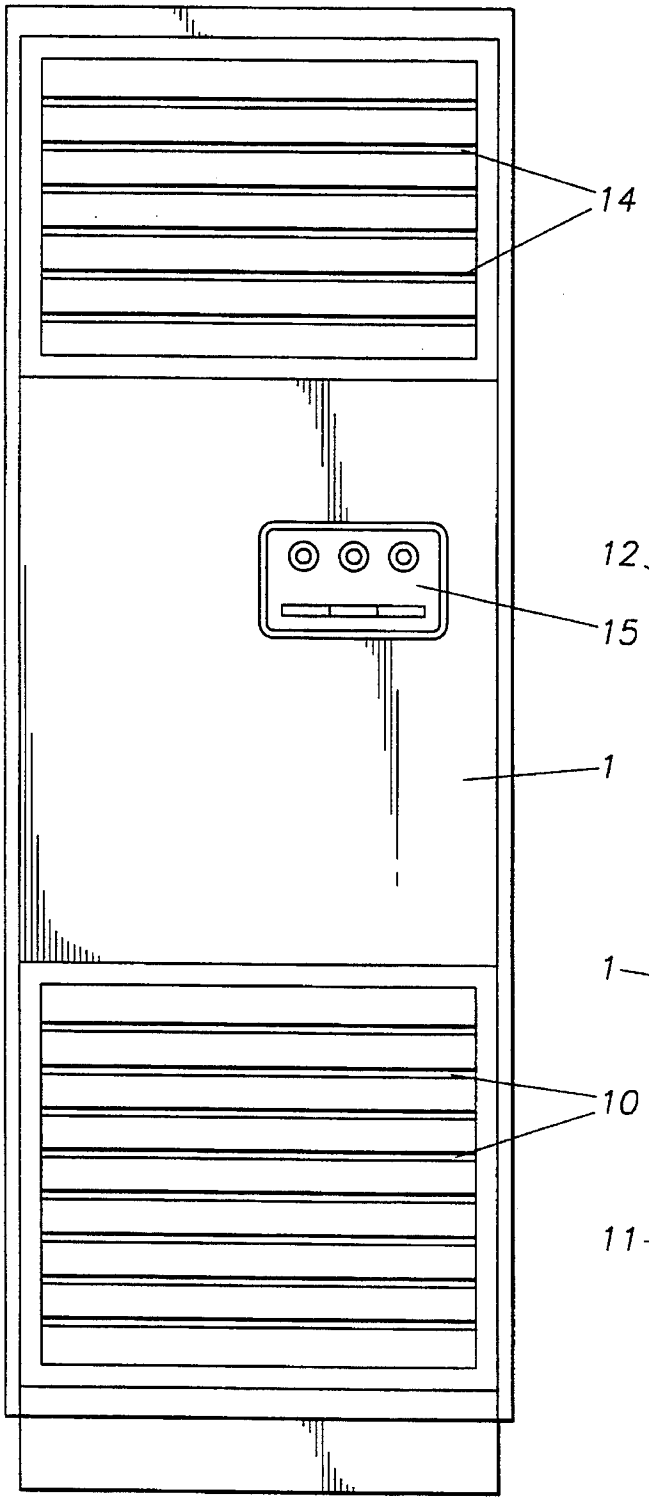
FIG. 11 (PRIOR ART)
FIG. 11 is a front view of an indoor unit according to the prior art.
Figure 12:
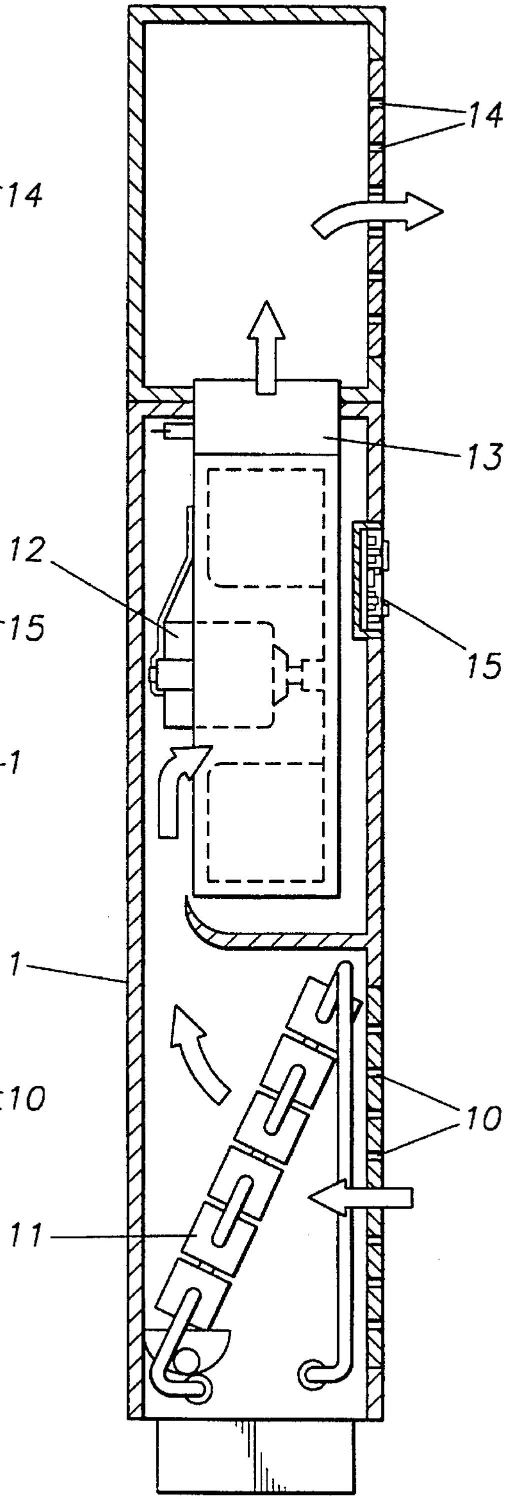
FIG. 12 (PRIOR ART)
FIG. 12 is a vertical cross-sectional view of the indoor unit shown in FIG. 11.
Figure 13:
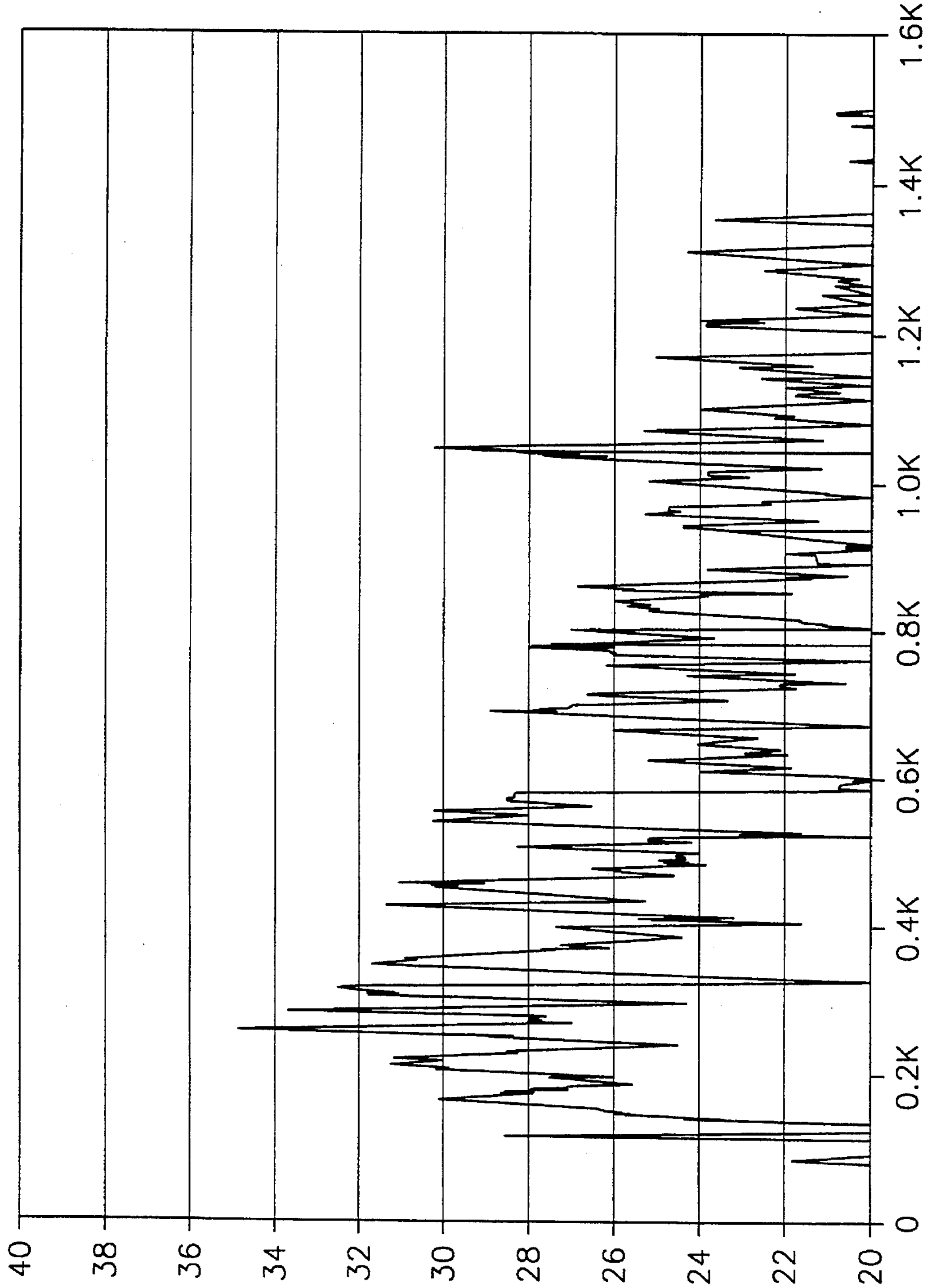
FIG. 13 (PRIOR ART)
FIG. 13 is a view illustrating a noise spectrum in the prior art indoor unit.
Figure 14A:
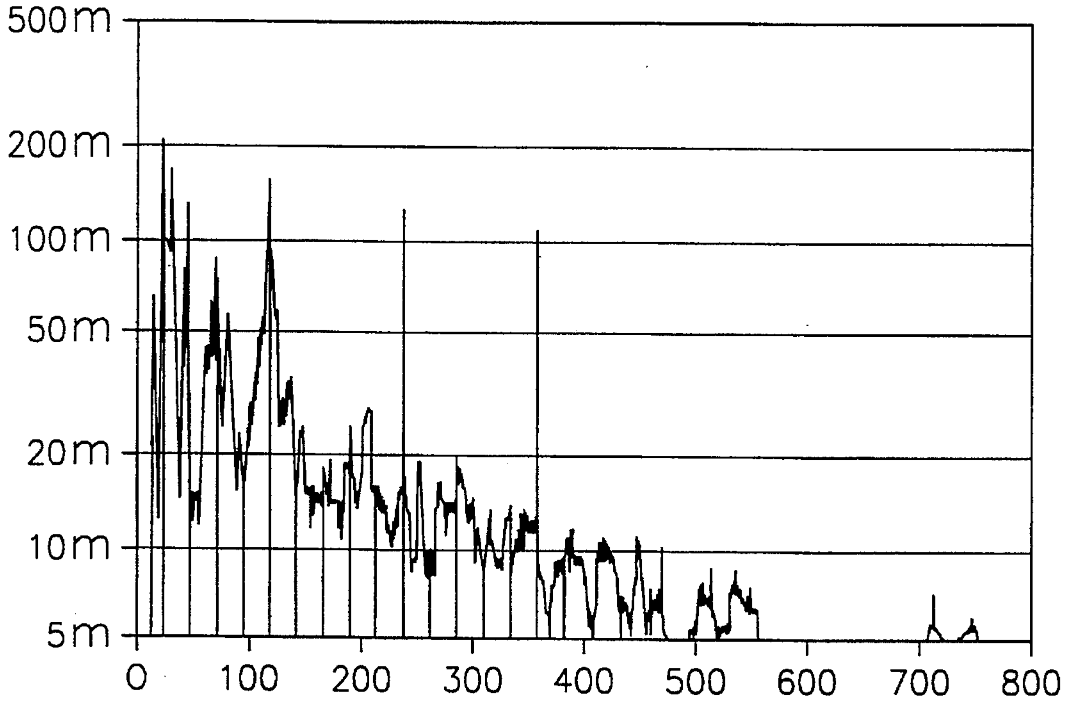
FIG. 14a (PRIOR ART)
FIG. 14 is a view illustrating a vibration spectrum in the prior art indoor unit.
Figure 14B:
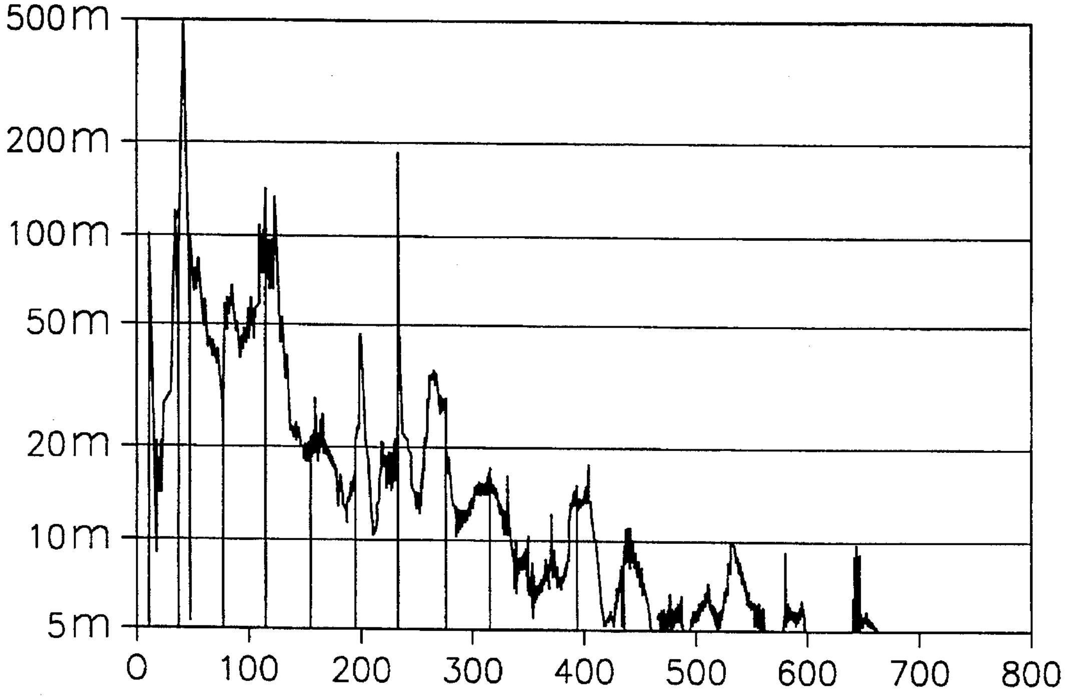
FIG. 14b (PRIOR ART)
Figure 15C:
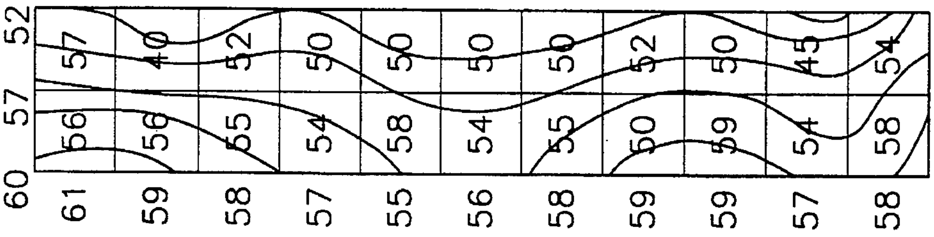
FIG. 15c (PRIOR ART)
FIG. 15 is a waveform chart of the noises generated at the left, the front and the right side of the prior art indoor unit.
Figure 15B:
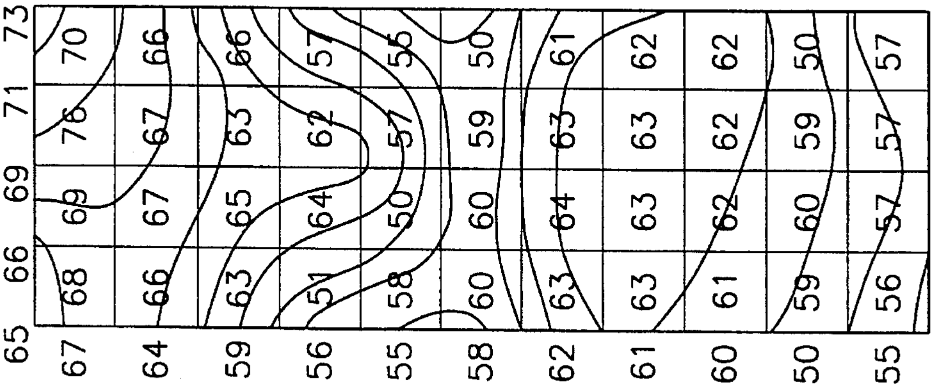
FIG. 15b (PRIOR ART)
Figure 15A:
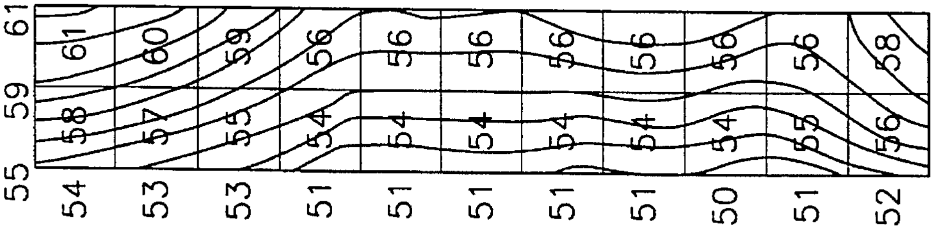
FIG. 15a (PRIOR ART)

With this construction, during operation of the indoor unit 1, a noise generated by flow of air discharged along the route comprising in turn an intake grid 10, a heat exchanger 11, the centrifugal fan 12, the exhaust duct 13 and the exhaust grid 14 is diminished through reduction of its low frequency band by a noise signal of an antiphase emitted from the upper and lower speakers 20 and 21. That is, when the noise generated at the indoor unit has a noise waveform with a time-domain as shown in FIG. 9A, attenuation effect by which the signal in FIG. 9A disappears may be accomplished by generating a signal, as shown in FIG. 9B, which is phased 180 degrees apart from the phase of the noise in FIG. 9A, but has the same magnitude as that of the noise.

Figure 5:
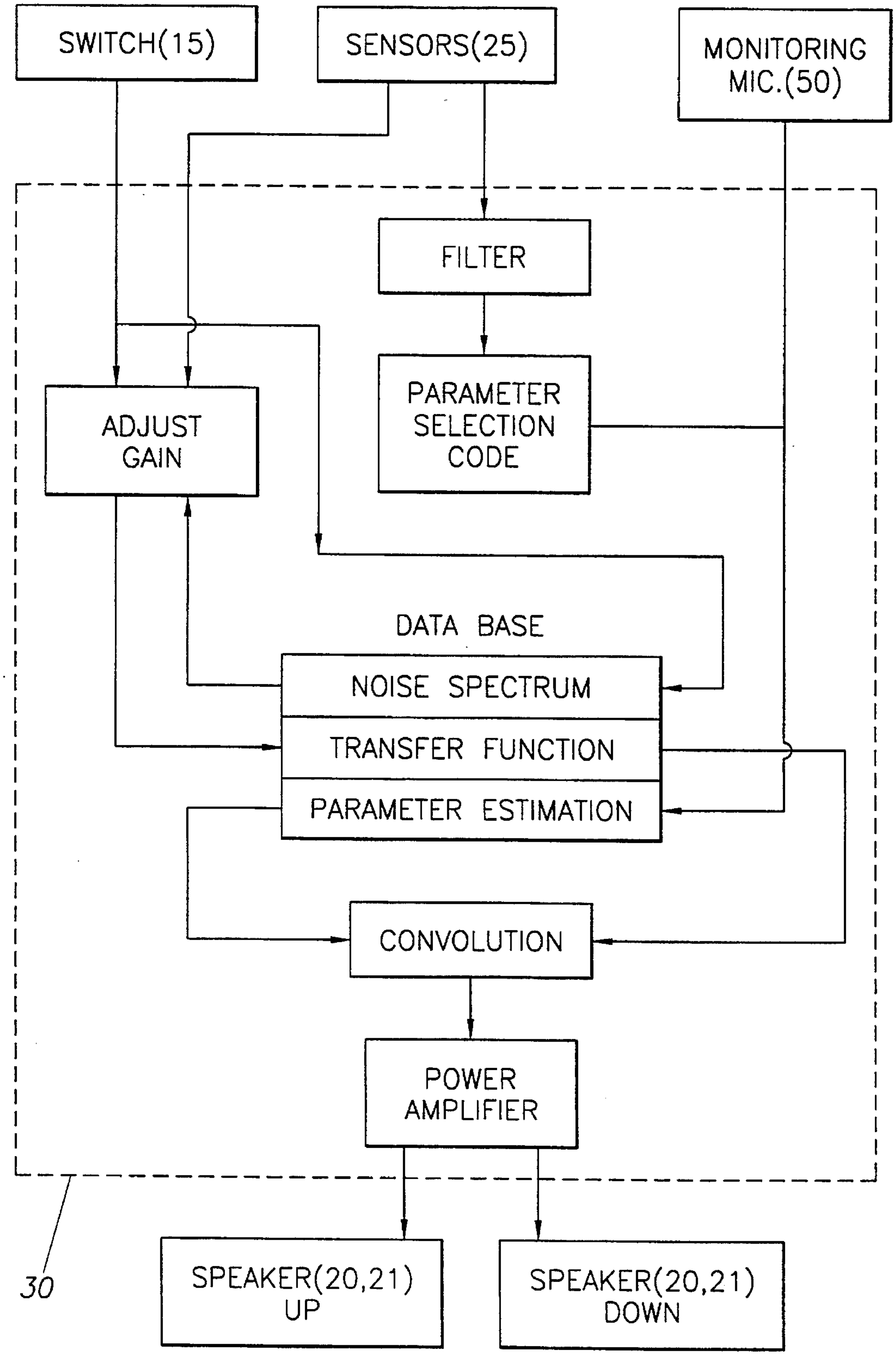
FIG. 5 is a logic flowchart of a control section being one of the principal parts of the present invention.

In order to emit such an antiphase signal through the upper and lower speakers 20 and 21, there is a need for a control section 30 which is control means performing functions as shown in a block diagram of FIG. 5. The control section 30 functions to receive the sensed noise condition from the sensor 25 disposed at a noise source, get a specific vibration noise spectrum depending upon air volume selection at the control panel 15, from a data base including a variety of noise spectra transfer functions and parameters, get a specific transfer function through gain adjustment of the vibration noise spectrum, the selected air volume and the sensed noise condition, convert the sensed noise into a parameter selection code by filtering the noise by a low-pass filter, convolute the transfer function and a designated parameter from the parameter selection code, thereby generating a signal, i.e., a control noise having an antiphase as opposed to the generated noise, amplify the signal, and emit the amplified signal through the upper and lower speakers 20 and 21. Thus, the energy of the noise emitted from the indoor unit may be diminished by the control noise, i.e., the antiphase signal emitted from the upper and lower speakers 20 and 21, thereby resulting in reduction of the noise.

Although the sensor 25 for sensing the noise condition may be of any of various types, the preferred embodiment of the present invention utilizes a vibration sensor which is able to sense vibration caused by the noise. This is for eliminating variation of factors affected by the surroundings when using a sensor having a microphone function.

Figure 3:
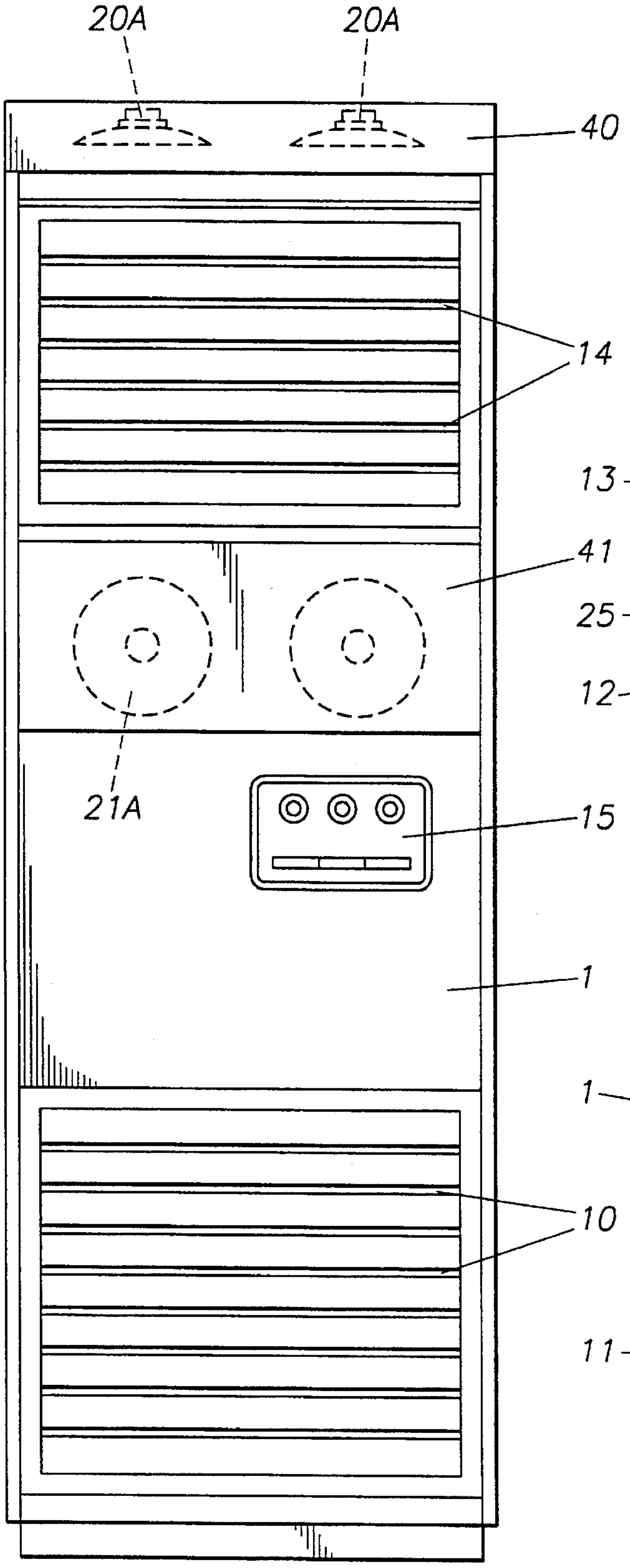
FIG. 3 is a front view of the indoor unit incorporating the device according to another embodiment of the present invention.
Figure 4:
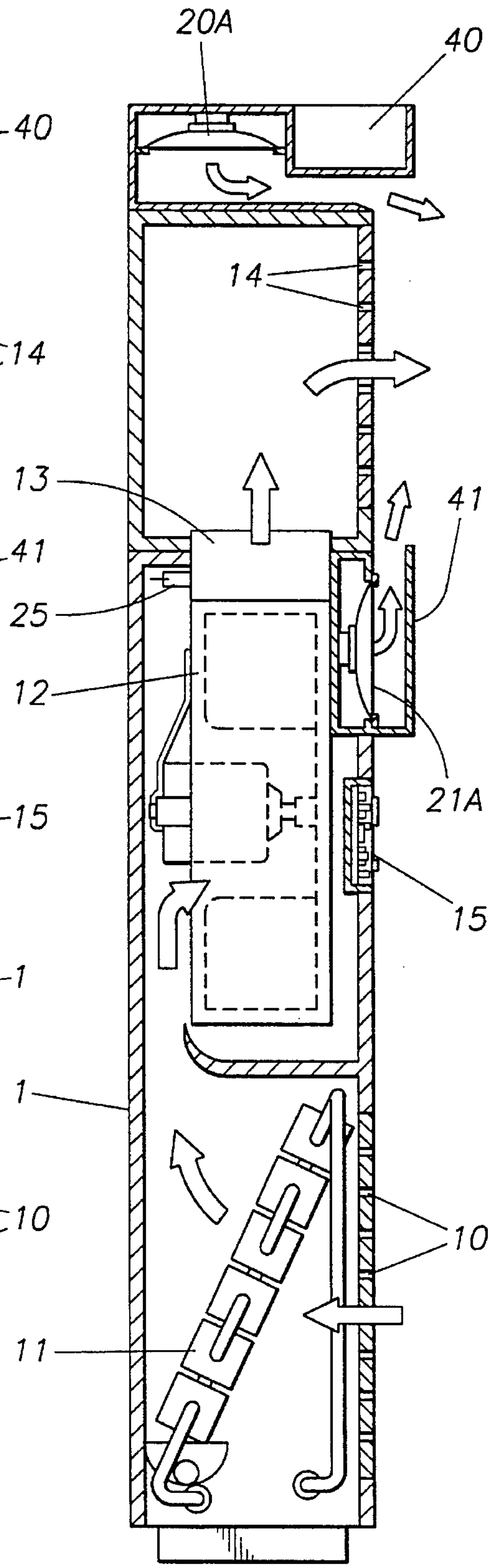
FIG. 4 is a vertical cross-sectional view of the indoor unit shown in FIG. 3.

FIGS. 3 and 4 illustrate the indoor unit according to another embodiment of the present invention, in which the basic construction of emitting the control noise by using the speakers is the same as that of the embodiment shown in FIGS. 1 and 2 except that the installation positions of the upper and lower speakers are varied.

While in the embodiment shown in FIG. 2 the upper and lower speakers 20 and 21 are mounted in front of the exhaust grid 14 in confronting relation to each other, the embodiment in FIG. 4 comprises upper horizontal and lower vertical noise ducts 40 and 41 disposed at the upper and lower speakers 20*a* and 21*a*, respectively, to guide the control noises emitted from the speakers. In addition, in this embodiment, the upper speaker 20*a* is horizontally disposed at the inner end of the upper horizontal noise duct provided on the top of the indoor unit, and the lower speaker 21*a* is vertically disposed within the lower vertical noise duct provided at the front side of the unit. Therefore, the control noise from the upper speaker 20*a* is emitted through the upper horizontal noise duct 40 in the same direction as the direction of flow of the air discharged through the exhaust grid, and the control noise from the lower speaker 21*a* is emitted through the lower vertical noise duct 41 in the direction perpendicular to the flow of the air discharged through the exhaust grid. The purpose of emitting the control noises through the noise ducts 40 and 41 is to enhance the noise control effect by concentrating the control noises emitted through the noise ducts and symmetrizing the discharging directions of the control noises with the noises generated at the upper and lower sides of the exhaust grid 14.

At this time, the optimal installation positions of the speakers or the optimal value of the control noise according to capacity of the indoor unit and conditions of the space to be air-conditioned may be obtained from the following equations expressed by modeling the speakers and the indoor unit.

Figure 6A:
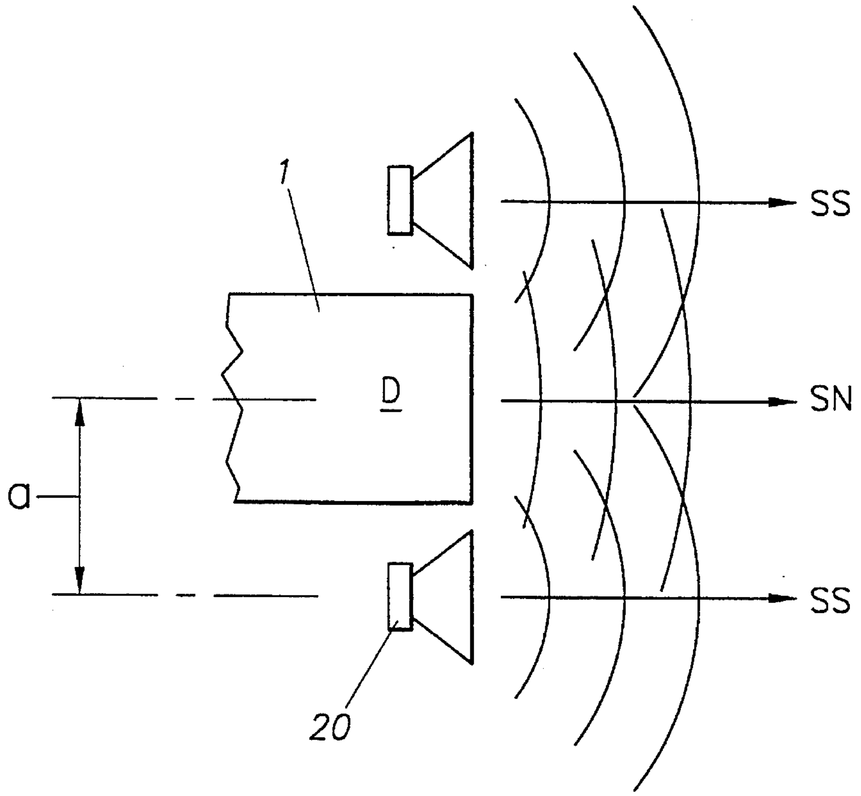
FIG. 6 is a diagrammatic view depicting the principle of the present invention analyzed through modeling work.
Figure 6B:
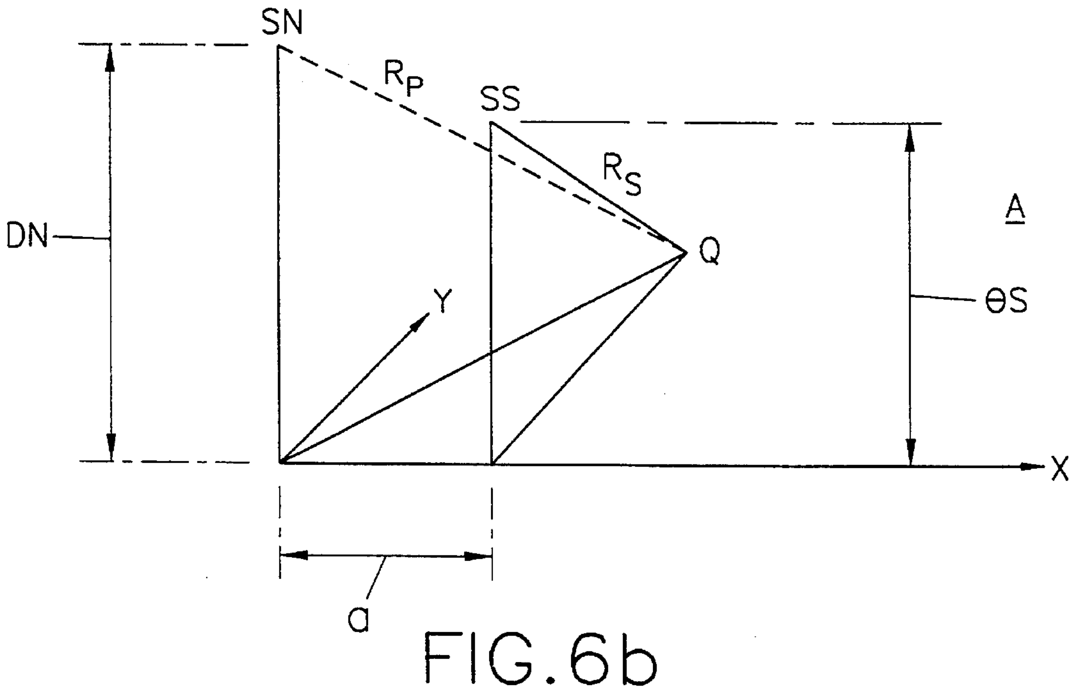

In the model shown in FIG. 6, the optimal amplitude of pressure generated between the noise source, SN, of the indoor unit and the control noise sources, SS, of the speakers is expressed by the following equation:

$$Pm=(1-Vm^2\iint\{1/R_S^2\}dA/\iint_A 1/R_p^2\}dA\ )^{1/2}$$

Here, if the space to be controlled is subdivided into spaces of n in number, the following equation is obtained:

$$Pm=\left(1-Vm^2\sum_{i=1}^{n}1/Rs\,(i)^2/\sum_{i=1}^{n}1/R_p^2(i)\right)^{1/2}$$

The minimal value of noise suppression may be obtained by comparing the values of the various factors of the data base in the control means on the basis of this equation.

The value, Vm, referred to the above equations is the value obtained from the following equation:

$$Vm=\frac{-\int_A\int(\{\cos(\alpha\cdot Rs-\alpha\cdot R_p+\Phi op)\}/R_p\cdot Rs\,dA)}{\int_A\int(1/Rs^2)\,dA}$$

Where, A: space for noise reduction (assumed to be a plane), $R_p$, Rs: distances from a noise source and a speaker to the space (A), W: angular frequency (=2πf), α: wave number (W/C; C is the speed of sound), Φ: phase difference between the noise and the sound generated by the speaker, Φ op: optimal value of Φ.

While the value of the denominator of the above equation represents the value of the noise emitted from the indoor unit, the value of the numerator represents the value of the control noise emitted from the speaker. In this case, in order to measure the value of the noise generated at the indoor unit, and then feed back the value as one factor for the control means, i.e., the control section 30, thereby looking for the optimal precise value, it is preferable to additionally include, as showing the circuit diagram of FIG. 5, a microphone 50 for sensing a condition of the final noise emitted from the indoor unit and subjected to the noise control operation.

Figure 7A:
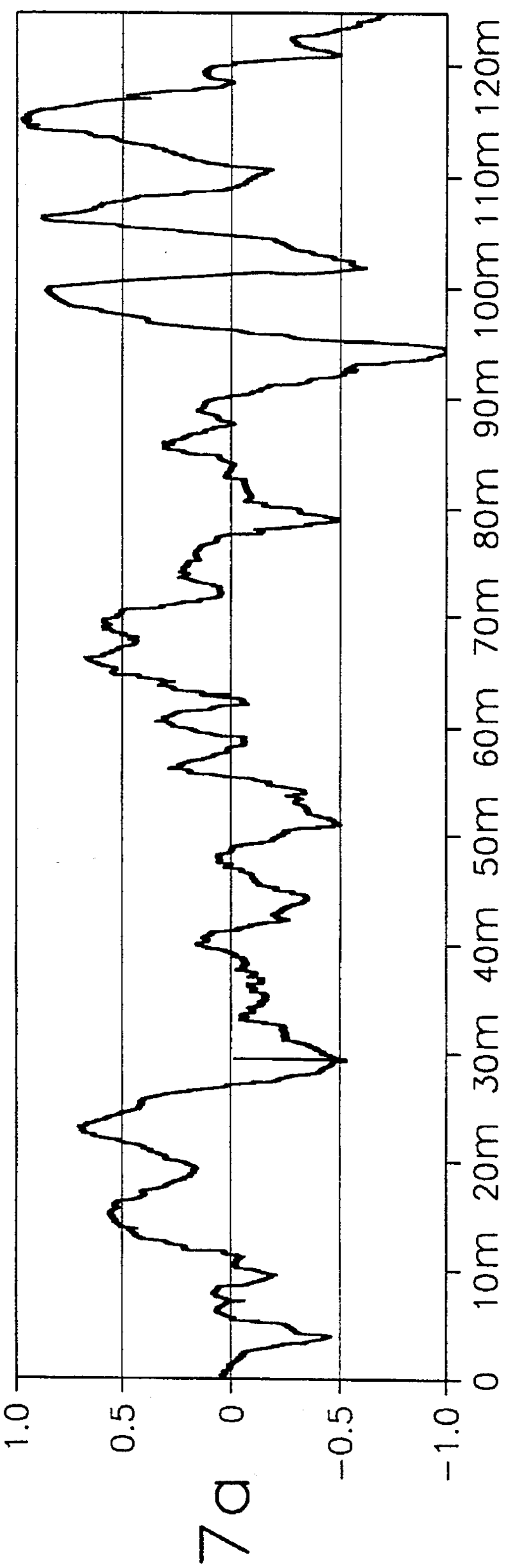
FIG. 7A is a real waveform chart of a noise generated at the indoor unit.
Figure 7B:
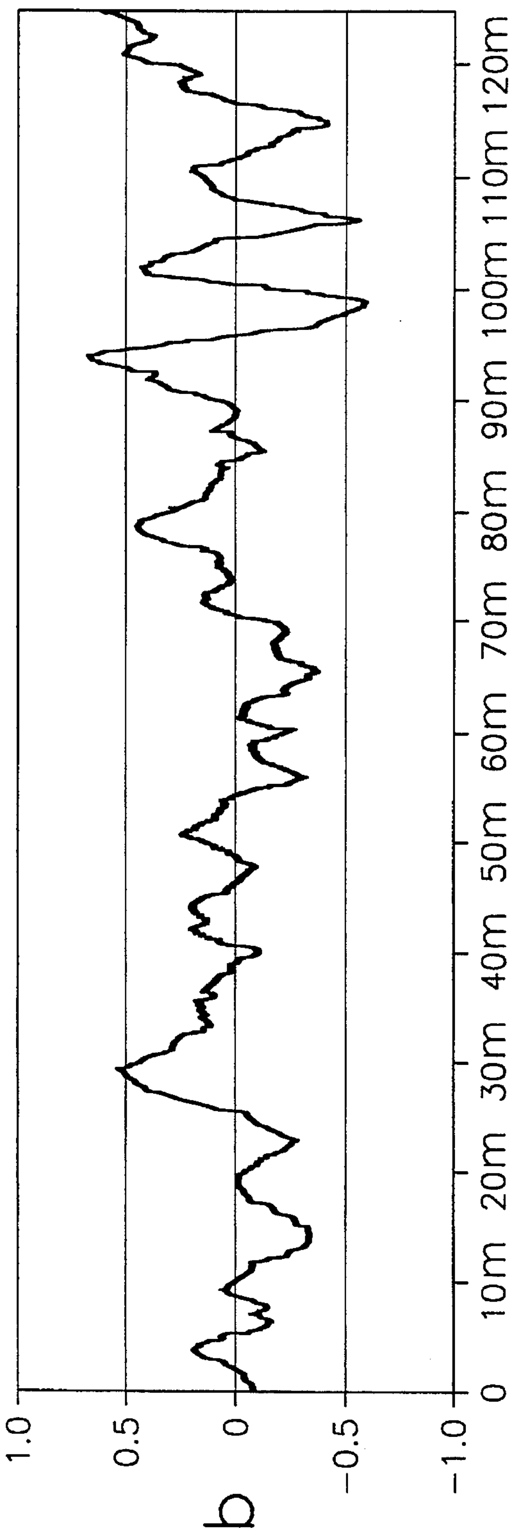
FIG. 7B is a real waveform chart of a control noise emitted from a speaker and having an antiphase as opposed to that in FIG. 7A.
Figure 8A:
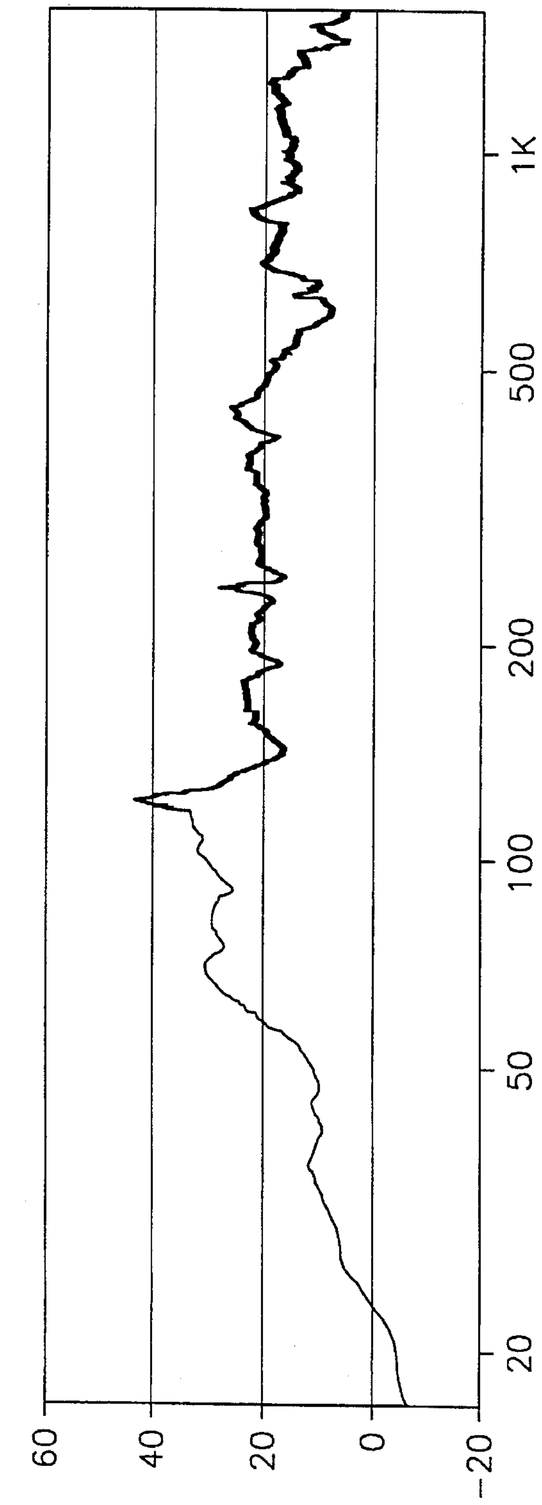
FIG. 8A is a waveform chart of the noise from the indoor unit provided with the device of the present invention, showing the state before the noise control operation.
Figure 8B:
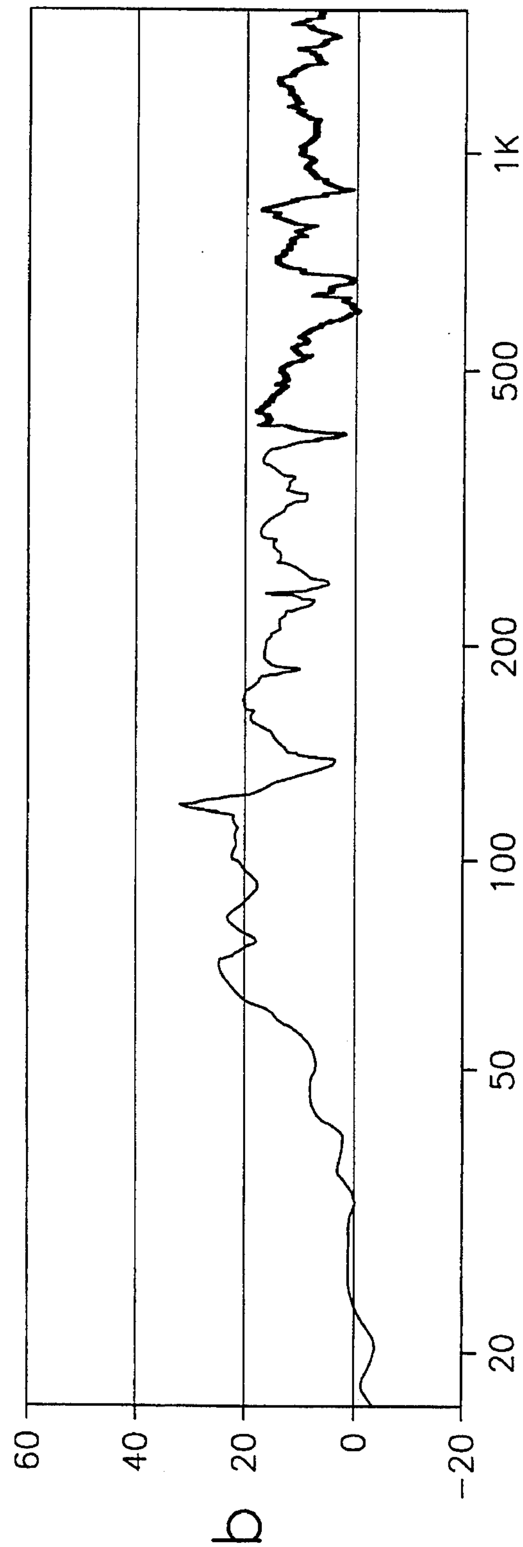
FIG. 8B is a waveform chart similar to FIG. 8A, but showing the state after the noise control operation.

The results of experimental measurements of the noise control state controlled in the manner described above indicate that emission of the antiphase signal as shown in FIG. 7B against the noise signal from the indoor unit as shown in FIG. 7A results in a noise suppression effect as will be apparent from the comparison of the waveform chart of the noise from the indoor unit before the noise control operation as shown in FIG. 8A with that after the noise control operation as shown in FIG. 8B. Thus, the present invention provides an advantage in that, since the noise having a low frequency band and emitted from the upper side of the indoor unit is reduced by emitting the control noise having an antiphase difference against the noise from the unit, the user may use the apparatus in an agreeable condition.

Having thus described a preferred embodiment of the present invention, it should be understood that the invention is not to be limited to the specific construction and arrangement shown. It will be apparent to those skilled in the art that modifications or alterations may be made without departing form the spirit of the invention as defined in the appended claims.

What is claimed is:

1. A method of reducing vibration noises generated at an indoor unit of a separate type room air conditioner device having a selectable speed fan, comprising the steps of:

selecting a fan speed of the air conditioner;

selecting a vibration noise spectrum from a data base containing predetermined data obtained under optimal conditions for each speed of the fan, said selecting being made according to the selected fan speed;

sensing a vibration noise from said air conditioner;

generating an actual vibration noise spectrum corresponding to said vibration noise and determining a parameter selection code representative of phase information of said vibration noise;

adjusting a gain between said vibration noise spectrum and said actual vibration noise spectrum and obtaining a transfer function representative of a frequency content of said vibration noise;

selecting a parameter from said data base according to said parameter selection code;

convoluting said parameter and said transfer function to produce a reverse-phased sound signal, wherein said sound signal is equal to said vibration noise; and generating a sound according to said reverse-phased sound signal and damping said vibration noise by interference between said vibration noise and said sound.

2. The method of claim 1, further comprising the steps of monitoring said damping and adjusting said parameter selecting code in accordance with a result of said monitoring residual noise after.

3. An apparatus for reducing vibration noises generated at an indoor unit of a separate type room air conditioner device having a selectable speed fan, comprising:

means for determining a selected fan speed of the air conditioner and for selecting a noise spectrum from a data base in accordance with said selected fan speed, said data base containing predetermined data obtained under an optimal conditions for each speed of the fan;

a vibration sensor for sensing a vibration noise in a duct of said air conditioner;

means for generating an actual vibration noise spectrum corresponding to said vibration noise and for determining a parameter selection code representative of phase information of said vibration noise;

means for adjusting a gain between said vibration noise spectrum and said actual vibration noise spectrum and for obtaining a transfer function representative of a frequency content of said vibration noise;

means for selecting a parameter from said data base according to said parameter selection code;

and convoluting said parameter and said transfer function to produce a reverse-phased sound signal, wherein said sound signal is equal to said vibration noise; and a pair of speakers disposed at an upper and a lower side of an exhaust grid of the air conditioner, for generating a sound according to said reverse-phased sound signal and damping said vibration noise by interference between said vibration noise and said sound.

4. The apparatus of claim 3, wherein said speakers are disposed facing each other such that said sound is generated in a direction perpendicular to an air exhaust direction.

5. The apparatus of claim 3, wherein the direction of one of said speakers is disposed perpendicular to the direction of the other said speaker such that said sound is generated in directions both perpendicular to an air exhaust direction and in the air exhaust direction.

6. The apparatus of claim 3, further comprising a microphone for sensing residual noise after damping for said and adjusting said parameter selecting code.

* * * * *

UNITED STATES PATENT AND TRADEMARK OFFICE
CERTIFICATE OF CORRECTION

PATENT NO. : 5,457,750

DATED : October 10, 1995

INVENTOR(S) : Byung H. Ahn

It is certified that error appears in the above-identified patent and that said Letters Patent is hereby corrected as shown below:

Column 5, line 38, replace "form" with --from--.

Column 6, line 13, insert --residual noise after-- between "monitoring" and "said";

Column 6, line 15, delete "residual noise after".

Column 6, line 37, replace "and" (1st. occu.) with --means for--.

Column 6, line 54, insert --said-- between "after" and "damping; insert --and-- between "damping" and "for"; and delete "said and".

Signed and Sealed this

Twenty-seventh Day of February, 1996

Attest:

Bruce Lehman

BRUCE LEHMAN

*Attesting Officer* *Commissioner of Patents and Trademarks*

UNITED STATES PATENT AND TRADEMARK OFFICE

CERTIFICATE OF CORRECTION

PATENT NO. : 5,457,750

DATED : October 10, 1995

INVENTOR(S) : Byung H. Ahn

It is certified that error appears in the above-identified patent and that said Letters Patent is hereby corrected as shown below:

Column 5, line 38, replace "form" with --from--.

Column 6, line 12, insert --residual noise after-- between "monitoring" and "said";

Column 6, line 14, delete "residual noise after".

Column 6, line 35, replace the first incidence of "and" with --means for--.

Column 6, line 52, insert --said-- between "after" and "damping"; insert --and-- between "damping" and "for"; and delete "said and".

This certificate supersedes Certificate of Correction issued February 27, 1996.

Signed and Sealed this

Twenty-fifth Day of June, 1996

Attest:

BRUCE LEHMAN

*Attesting Officer* *Commissioner of Patents and Trademarks*